(12) United States Patent
DeFranks et al.

(10) Patent No.: US 9,640,167 B2
(45) Date of Patent: May 2, 2017

(54) SMART PILLOWS AND PROCESSES FOR PROVIDING ACTIVE NOISE CANCELLATION AND BIOFEEDBACK

(71) Applicant: DREAMWELL, LTD, Las Vegas, NV (US)

(72) Inventors: Michael S. DeFranks, Atlanta, GA (US); Michael A. Golin, Atlanta, GA (US)

(73) Assignee: DREAMWELL, LTD, Las Vegas, NV (US)

( * ) Notice: Subject to any disclaimer, the term of this patent is extended or adjusted under 35 U.S.C. 154(b) by 14 days.

(21) Appl. No.: 14/830,764

(22) Filed: Aug. 20, 2015

(65) Prior Publication Data

US 2016/0055842 A1 Feb. 25, 2016

Related U.S. Application Data

(60) Provisional application No. 62/039,515, filed on Aug. 20, 2014.

(51) Int. Cl.

| | |
|---|---|
| G10K 11/16 | (2006.01) |
| H04B 3/20 | (2006.01) |
| G10K 11/175 | (2006.01) |
| A47G 9/10 | (2006.01) |
| G10K 11/178 | (2006.01) |
| A47G 9/00 | (2006.01) |

(52) U.S. Cl.
CPC ............ *G10K 11/175* (2013.01); *A47G 9/10* (2013.01); *G10K 11/1786* (2013.01); *A47G 2009/006* (2013.01); *A47G 2009/1018* (2013.01); *G10K 2210/116* (2013.01); *G10K 2210/3027* (2013.01); *G10K 2210/3044* (2013.01); *G10K 2210/3221* (2013.01); *G10K 2210/505* (2013.01)

(58) Field of Classification Search
CPC ................ A47G 9/10; A47G 2009/006; A47G 2009/1018; G10K 2210/505; G10K 2210/116; G10K 11/175; G10K 2210/3027; G10K 2210/3044; G10K 11/1786; G10K 2210/3221; G10K 11/178
See application file for complete search history.

(56) References Cited

U.S. PATENT DOCUMENTS

| | | | | |
|---|---|---|---|---|
| 5,844,996 A | * | 12/1998 | Enzmann | ............. A61B 5/7475 381/71.11 |
| 7,674,224 B2 | | 3/2010 | Hewett | |
| 8,325,934 B2 | | 12/2012 | Kuo | |
| 2009/0147965 A1 | * | 6/2009 | Kuo | .................... A47C 21/003 381/71.6 |
| 2010/0302044 A1 | * | 12/2010 | Chacon | .................... A61F 5/56 340/575 |

(Continued)

FOREIGN PATENT DOCUMENTS

WO 2014083375 A1 6/2014

OTHER PUBLICATIONS

Hughes, Charlie., "Sum & Difference Frequencies", Excelsior Audio Design & Services: Jun. 25, 2014; pp. 1-2.

(Continued)

*Primary Examiner* — Muhammad N Edun
(74) *Attorney, Agent, or Firm* — Cantor Colburn LLP

(57) ABSTRACT

A smart pillow unit and processes for providing active noise cancellation and biofeedback.

21 Claims, 4 Drawing Sheets

(56) References Cited

U.S. PATENT DOCUMENTS

| | | | |
|---|---|---|---|
| 2012/0163626 A1* | 6/2012 | Booij | G10K 11/1788 381/92 |
| 2013/0204617 A1 | 8/2013 | Kuo et al. | |
| 2014/0169580 A1* | 6/2014 | Levitov | G10K 11/178 381/71.6 |

OTHER PUBLICATIONS

Marshall, Lisa., "Boosting slow oscillations during sleep potentiates memory", Nature: Nov. 2006; vol. 440, pp. 610-613.
Tononi, G., "Enhancing Sleep Slow Waves With Natural Stimuli", MedicaMundi: 2006; vol. 54:2, pp. 82-88.

\* cited by examiner

SMART PILLOWS AND PROCESSES FOR PROVIDING ACTIVE NOISE CANCELLATION AND BIOFEEDBACK

CROSS REFERENCE TO RELATED APPLICATIONS

This application is a NON-PROVISIONAL of and claims the benefit of U.S. application Ser. No. 62/039,515, filed Aug. 20, 2014, which is incorporated herein by reference in its entirety.

BACKGROUND

The present disclosure generally relates to pillows and more particularly, an active noise control and biofeedback system integrated with the pillow for improving sleep quality. The biofeedback component delivers frequencies configured to enhance sleep quality and stimulate slow wave sleep.

The sonic environment around a sleeper can have dramatic effects on their ability to fall asleep and stay asleep. Noise disturbances affect a significant portion of the population. In a 2011 study by the National Sleep Foundation, 41% of respondents claimed that partner snoring had a large effect on their ability to sleep at night. In fact, it is estimated that approximately 40% of males and 25% of females snore periodically. In order to promote a sleeping environment that can positively affect sleep quality, the issue of snoring partners must be tackled.

There are several current solutions for the snoring partner issue. USA Today estimates that 27% of couples over age 40 occasionally sleep in separate bedrooms to escape snoring. In addition, white noise machines have been used to drown out the snoring of a partner and earplugs can be used to attenuate the snoring volume; however, none of these solutions are ideal. Sleeping in separate bedrooms is not a sustainable practice for most couples. White noise machines increase the total noise volume in the room as a way to mask snoring. Earplugs and earmuffs can be used to attenuate all incoming noise but can be ineffective for louder noises and/or uncomfortable. Moreover, the use of earplugs or earmuffs could pose a problem with hearing alarms and/or individuals at a distance from the user, e.g., small children. Noise cancelling headphones, e.g., QuietComfort™ headphones commercially available from the Bose Corporation, are available on the market but like earmuffs pose discomfort issues when worn to bed.

Many consumer product companies have developed ways of incorporating biofeedback into products. Smartphone and computer applications have been developed to play soothing sounds and music with the purpose of initiating sleep; however, these products do not have effective ways of delivering the music to the sleeper as they must rely on the Smartphone speakers, headphones or computer speakers.

BRIEF SUMMARY

Disclosed herein are methods for providing a smart pillow with noise cancellation or abatement in combination with biofeedback. The smart pillow includes speakers, microphones and wireless communication to provide a combination of functions novel to the product. The smart pillow would not only use advanced technology to decrease the audible presence of snoring from partners but also use the same sound delivery system to improve quality of sleep through biofeedback.

Biofeedback can take the form of an entrainment sound to influence the brain's state. The human brain produces electrical signals with systematic regularity. Brain waves are produced at consistent frequencies according to the state of consciousness and unconsciousness. Brain entrainment is the technique of instigating specific frequencies of brain activity through external stimuli in order to drive a specified brain state.

The system would be capable of playing music and sounds specifically designed to improve sleep quality, e.g., decrease sleep onset latency, increase sleep time, decrease the number of apnea and/or arousal events, increase sleep efficiency, various combinations thereof, and the like. The system would also be capable of delivering a specified arrangement of music designed to calm the user and help them relax. The music could help the user control their breathing patterns and heart rate to initiate sleep. The system could also be used to deliver sounds at frequencies designed to stimulate Slow Wave Sleep, helping the user enter deep sleep faster and stay in deep sleep longer. As used herein, slow waves are generally defined as high amplitude electroencephalographic waves (>50 microvolts) that occur once every second or so during deep non-rapid eye movement. The longer one has been awake, the more frequent and larger are the slow waves during sleep. Conversely, slow waves become fewer and smaller the more time one spends asleep. The slow wave stimuli could also turn off during the night so as to not disturb the user as they shift to more REM heavy periods of sleep; although, ideally the system would be synched to adapt dynamically based upon the subject's sleep stage as determined by a sleep monitor or sensor, which may be imbedded in the pillow, mattress, foundation or the like or optionally may be worn by the user (e.g., MotionX 24/7, Jawbone UP24, EarlySense or similar device).

In one embodiment, a process for providing active noise cancellation and biofeedback in an electronic pillow comprising a pillow unit operatively coupled to a reference sensing unit and a controller unit comprises receiving signals via a plurality of error microphones encased in the pillow unit, wherein the error microphones are spaced a first predetermined distance from one another; receiving at least one signal from at least one reference sensing microphone in the reference sensing unit; and processing signals received from the error microphones and reference sensing microphone in the controller unit to simultaneously reduce noise and provide biofeedback in an area between the error microphones using a plurality of speakers encased in the pillow unit, where each of the speakers are spaced a second predetermined distance from each of the respective error microphones, wherein noise is reduced in the controller unit utilizing a multiple-channel feed-forward active noise control, and wherein the controller unit processes signals received from the at least one of the error microphones and an external source simultaneously provide both acoustic echo cancellation and biofeedback, wherein the biofeedback comprises emitting a sound at frequencies of less than 2.0 Hz by using constructive and/or destructive interference patterns of higher frequency sound waves or volume modulation of source content from at least one of the plurality of speakers.

In another embodiment, the process for providing active noise cancellation and biofeedback comprises receiving signals via a plurality of error microphones encased in the pillow unit, wherein the error microphones are spaced a first predetermined distance from one another; receiving at least one signal from at least one reference sensing microphone in the reference sensing unit; and processing signals received from the error microphones and reference sensing microphone in the controller unit to simultaneously reduce noise and provide biofeedback in an area between the error microphones using a plurality of speakers encased in the pillow unit, where each of the speakers are spaced a second predetermined distance from each of the respective error microphones, wherein noise is reduced in the controller unit utilizing a multiple-channel feed-forward active noise control, and wherein the controller unit processes signals received from the at least one of the error microphones and an external source simultaneously provide both acoustic echo cancellation and biofeedback, wherein the biofeedback comprises providing entrainment frequencies with user defined music, wherein providing the entrainment frequencies comprises key masking the user defined music by determining a musical key of the user defined music and adjusting base frequencies of the entrainment frequencies so as to blend the entrainment frequencies with the user defined music.

The advantages of this system are its ability to actively cancel unwanted noise as well as provide soothing noises and sounds shown to improve sleep quality. The pillow would decrease disturbances as well as provide active benefits.

The disclosure may be understood more readily by reference to the following detailed description of the various features of the disclosure and the examples included therein.

BRIEF DESCRIPTION OF THE SEVERAL VIEWS OF THE DRAWINGS

Referring now to the figures wherein the like elements are numbered alike.

DETAILED DESCRIPTION

Figure 1:
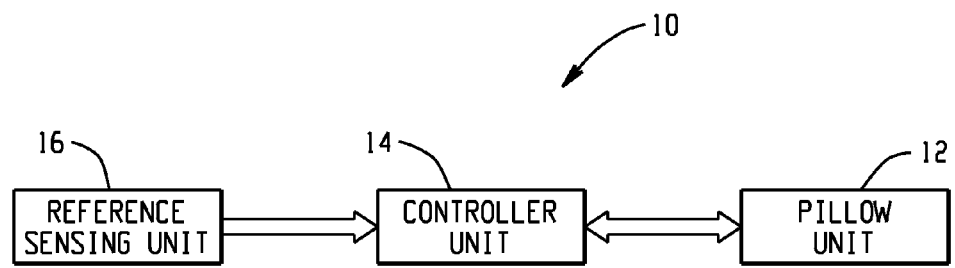
FIG. 1 is a block diagram of the electronic pillow including a pillow unit, controller unit, and reference sensing unit.

The present disclosure is generally directed to a smart pillow configured to provide active noise cancellation or abatement in combination with biofeedback. An exemplary smart pillow generally designated by reference numeral 10 is shown in the figures. The smart pillow 10 generally includes three main units: a pillow unit 12 in electrical connection with a controller unit 14 and a reference sensing unit 16 shown generally in FIG. 1 and as is generally described in U.S. Pat. No. 8,325,934, incorporated herein by reference in its entirety. The smart pillow 10 is portable, can be used in different bedrooms, different sides of the bed, and enables the user to receive the benefits of the pillow when traveling. Moreover, the smart pillow and related system can be configured to be used in combination with at least one additional smart pillow and at least one additional user as may be desired for different applications. In this manner, a pair of smart pillow systems can be used by two side by side sleeping partners, wherein the system may be configured to cancel out offending sounds produced by the partner's pillow including the biofeedback provided thereto (i.e. symmetrical functionality of a pair of pillows rather than one sensing pillow and one cancelling pillow), e.g., music and slow wave stimuli as will be described in greater detail below.

Each pillow unit 12 is more generally a pillow 18 that can be of any size desired to fit different sizes of pillowcases, thus the pillow 18 can match any bed. The pillow 18 can alternatively be in the form of a headrest for a chair depending on the use of the electronic pillow 10. For example, the pillow 18 can be a headrest for a chair in the home (an armchair), a plane seat, a train seat, or a car seat when being used for hands-free communications. The pillow 18 can be portable as described above and designed to be attachable to a chair, or it can be built directly into the chair as the headrest. Preferably, the pillow 18 is made of memory foam, but other fillers can also be used. The pillow 18 also encases at least one error microphone 20 and at least one loudspeaker 22 that are in electrical connection with the controller unit 14 as shown in FIG. 2.

Figure 2:
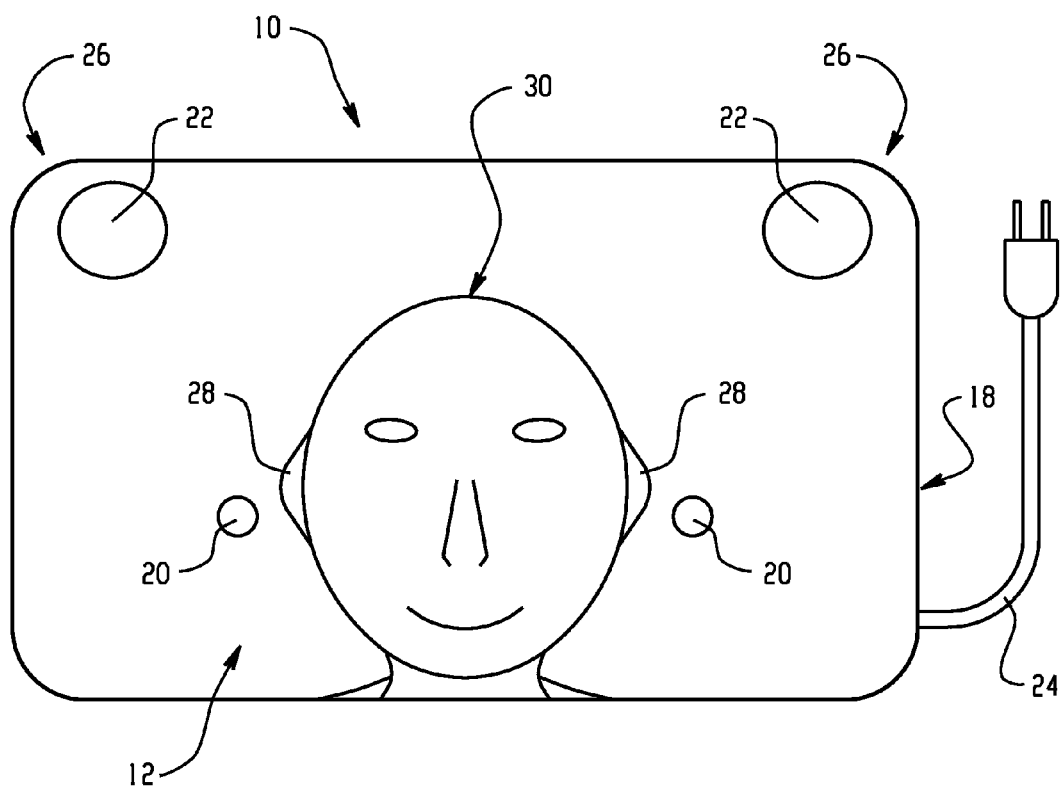
FIG. 2 is a top down schematic view of the electronic pillow and pillow unit.

In one embodiment, there are two error microphones 20 encased by the pillow 18, each positioned to be close to ears 28 of a user 30 as shown in FIG. 2. The error microphones 20 detect various signals or noises created by a user 30 and relay these signals to the controller unit 14 for processing. For example, the error microphones 20 can detect speech sounds from the user when the electronic pillow 10 is used as a hands-free communication device. The error microphones 20 also can detect noises that the user 30 hears, such as snoring or other environmental noises when the electronic pillow 10 is used for active noise cancellation and abatement. The quiet zone created by active noise cancellation and abatement is centered at the error microphones 20. Placing the error microphones 20 inside the pillow 18 below the user's 30 ears 28, generally around a middle third of the pillow 18, guarantees that the user 30 is close to the center of a quiet zone that has a higher degree of noise reduction than the prior art. In one embodiment, there are two loudspeakers 22 encased by the pillow 18, each in an upper back corner 26 of the pillow 18 relatively close to the user's 30 ears 28 as shown in FIG. 2. More or fewer loudspeakers 22 can be used depending on the desired function of the electronic pillow 10. The loudspeakers 22 function to produce various sounds for active noise control and for biofeedback. Additionally, the loudspeakers 22 may be configured to produce speech sound when electronic pillow 10 acts as a hands-free communication device, produce a warning sound when the electronic pillow 10 acts as a medical monitoring device, and/or produce audio sound for entertainment or masking of residual noise.

In this manner, the smart pillow 10 would not only decrease unwanted noise but produce sounds with the added functionality of improving one's quality of sleep, i.e., provide biofeedback. By way of example, the Concord Music Group has developed a suite of music arrangements shown to improve sleep quality and decrease sleep onset latency. The selected music works through biofeedback, providing audio stimuli to the body to entrain the subject's brain into falling asleep more quickly. Music selected through the Concord Music Group profile would be administered to the user through the loudspeakers 22 by way of a Smartphone application, for example.

This same application could also provide additional pulse frequencies of less than 2.0 Hz to further enhance sleep quality. In some embodiments, these pulse frequencies may be administered with sounds developed to improve sleep quality and decrease sleep onset latency. Slow Wave Sleep can be enhanced by use of external stimuli by introducing sound waves consistent with slow wave brain frequencies (see attachment by G. Tononi, *Enhancing Sleep Slow Waves with Natural Stimuli*, incorporated herein by reference in its entirety). Frequencies of less than 2.0 Hz are extremely difficult to produce with enough energy on their own; however, it is possible to create a beat frequency of less than 2.0 Hz by using constructive/destructive interference patterns of higher frequency sound waves.

There are several techniques which can be implemented to create an entrainment sound. Monaural, binaural and isochronic beats such as those discussed above can be used as well as modulations. Modulations can include but are not intended to be limited to, frequency, panning, reverb and volume.

Figure 4:
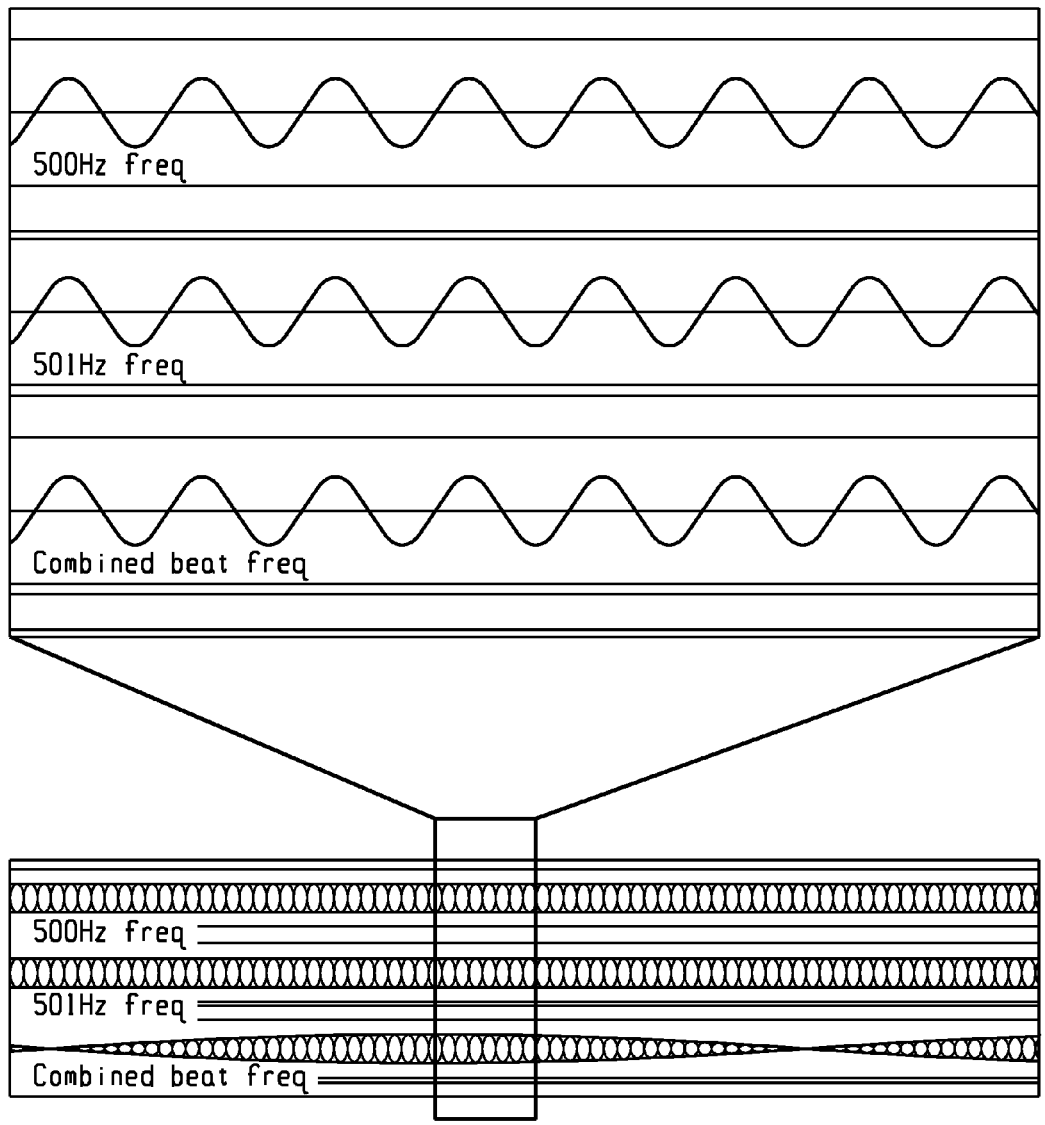
FIG. 4 is a diagram of an exemplary constructive and destructive interference patterns of frequencies producing a beat frequency.

When waves of two different frequencies are combined and out of phase they will produce a pattern of beats corresponding to their frequency differences. For example, if a 500 Hz and 501 Hz frequency are played together they will create a beat pattern of 1 Hz. The resultant sound will be beats of 500 Hz and 501 Hz occurring every one (1) second (see Excelsior Audio Design, *Sum and Difference Frequencies*). FIG. 4 is a diagram of the 500 and 501 Hz frequencies and the resulting constructive and destructive interference patterns produced from the combination of these frequencies to produce the 1 Hz beat frequency. Beat frequencies of less than 2.0 Hz may be applied through monaural frequency stacking in which both frequencies are combined into each speaker channel producing a beat frequency through each channel.

Other examples include isochronic tones such as a 50 millisecond (ms) segment of a 200 Hz tone alternated with 950 ms of silence yields a 1 hz presentation rate or, a 50 ms segment of a 200 Hz tone alternated with 450 ms of silence to yield a 2 hz frequency. Frequencies of 1 Hz are below the limits of human hearing; however, they are still registered by the brain and produce brain waves of 1 Hz. These brain waves entrain the auditory systems of the brain to generate 1 Hz brain waves initiating and/or extending slow wave sleep.

Figure 5:
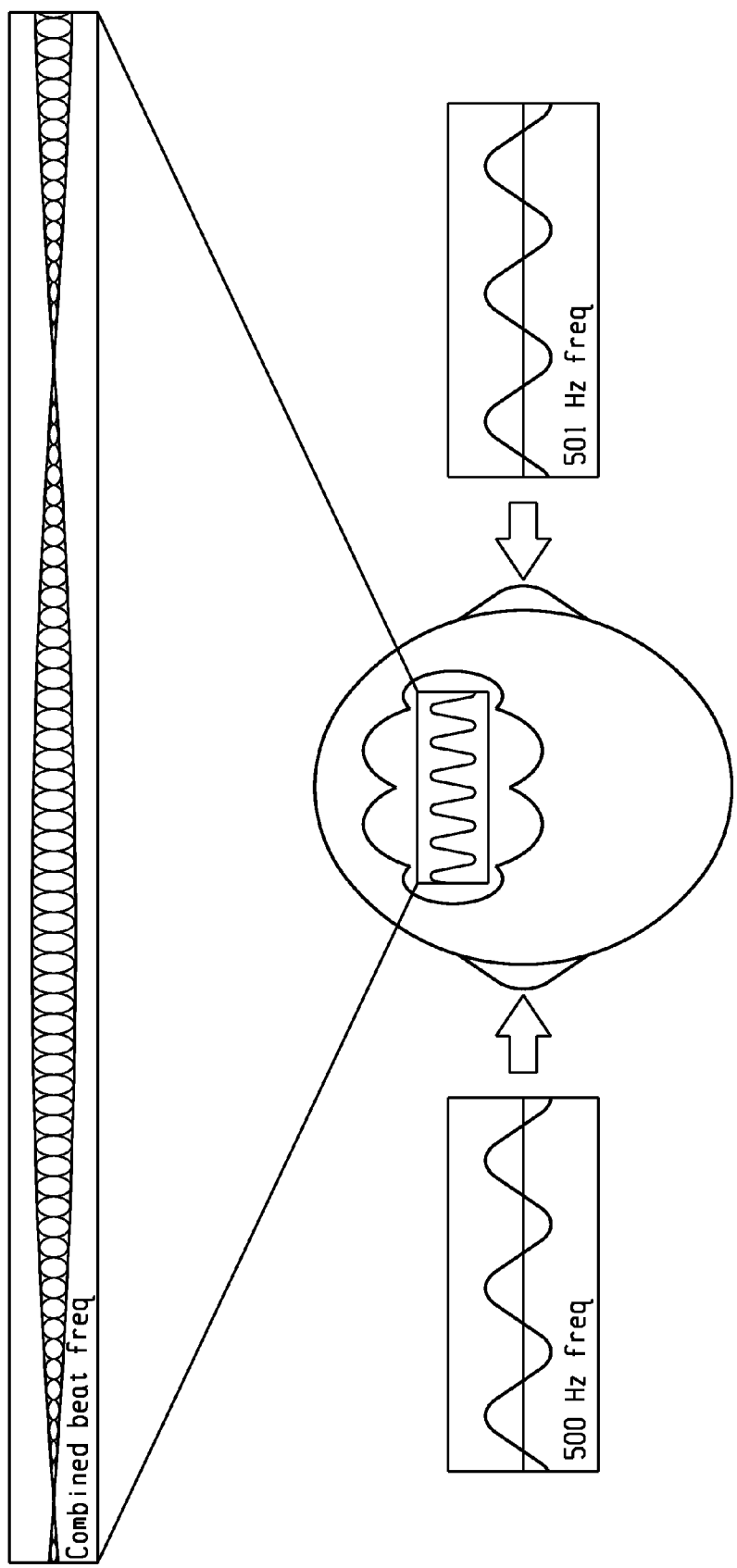
FIG. 5 is a diagram of the binaural effect of applying frequencies to different ears of a use.

Beat frequencies may also be produced through binaural combination in which the frequency pairs are split into left and right channels. FIG. 5 is a diagram of the binaural effect of applying the 500 and 501 Hz frequencies to different ears. The frequency summation (i.e., combined 1 Hz beat frequency) then occurs in the brain rather than the physical speaker system. Because it may be undesirable to only have sine wave frequencies produced, the very low frequency beat can be disguised within other program material such as described above and provided by Concord Music Group, thereby increasing sleep quality. The music may also employ a low pass filter volume modulation in which all frequencies below the low pass threshold are modulated at a frequency of less than 2.0 Hz while all frequencies above the threshold are unaltered. This process can also be used to entrain slow wave sleep brain activity. Any of the techniques for implementing an entrainment frequency can be conducted by a software application associated with a smartphone, computer, tablet or other electronic device. They may also be incorporated into the DSP of the pillow allowing the user to supply any desired music or sound content for processing from the source of the user's choice.

To minimize disruption possibilities of monaural, binaural or isochronic beats, these beats may be masked into program music. In one embodiment, the program music may be generated with these beats already implemented in order to match the base frequency of the entrainment technique with the program music. However, the implementation of preselected beats into user defined music could, in some instances, result in frequencies being out of tune with the existing program music causing dissonant notes that could be disruptive to the user.

In an alternative embodiment, the entrainment frequencies may be employed in conjunction with user defined music, which would provide a method of delivering brain entrainment without disruption as noted above. In this embodiment, in order to mask the entrainment method into program music effectively, the first step generally includes determining the musical key of the program music. A key determining algorithm can be utilized to select and adjust base frequencies for monaural, binaural or isochronic beats so that they blend with user defined program music.

By way of example, western music key can be determined through use of a fast fourier transform (FFT) function measuring the relative power of all frequencies captured within a recording. Sample rates for the FFT can be determined by the Nyquist-Shannon theorem in which the sample rate should be at least twice the highest frequency measured. Once the relative powers of all frequencies are measured, there are several methods available to those skilled in the art by which the key of a song can be determined. Common methods include root note determinacy, Krumhansl-Schmuckler, Temperley-Kotska-Payne, and the like. These methods use a combination of decision matrices including key profiling and Bayesian modeling with which to determine probability of a song key. The FFT function can be operated in short time segments of less than 100 ms. These short time segments can be individually analyzed with the results combined to give greater reliability to the key detection algorithm. Program music in the digital realm can be evaluated and processed through buffering which will allow the application to superimpose the entrainment frequencies in time with the music. This process of buffering and looking ahead allows the application to properly address key modulation in which the key of a song changes as the song progresses.

As such, the entrainment method could use any established key determining methods to extract the root or dominant frequency in the song at any point. The application would then superimpose a sine wave tone equivalent to the root note frequency (f1) of the song key as well as a sine wave tone offset from the root note by a specified frequency (f2) determined by the desired entrainment frequency of (f1-f2). The best range in which to set the base frequencies would be between 80-320 Hz, frequencies below this range may be difficult to produce with smaller speakers. Frequencies above 320 Hz could interfere with the song melody causing disruption to the user. By tuning the sine wave in accordance with the song key the superimposed tone would blend with the music. This would allow a user to define the set of songs within which to incorporate brain entrainment frequencies. The entrainment frequency can be selected according to the brain wave activity it is intended to stimulate. Through this technique the brain entrainment frequencies may be administered by way of monaural, binaural, isochronic beats or any combination of these.

Allowing the application to measure the key frequency and superimpose the entrainment frequencies onto the music solves the problem of detuned notes as previously discussed. With the superimposed notes in tune with the program music the entrainment program can remain masked by the user defined program music while still providing all of the benefits afforded to brain entrainment.

The loudspeakers 22 are generally small enough so as not to be noticeable by the user 30 when resting upon the pillow 18. In some embodiments, the loudspeakers may be in the form of a flexible circuit.

In some applications, there may be advantages to placing the loudspeakers 22 inside the pillow 18 relatively close to ears 28 of a user. The level of sound and anti-noise generated by the loudspeakers 22 are reduced compared to prior art devices, in which loudspeakers are placed above a user on a headboard of a bed. Lower noise levels also reduce power consumption and reduce undesired acoustic feedback from the loudspeakers 22 back to the reference sensing unit 16.

Figure 3:
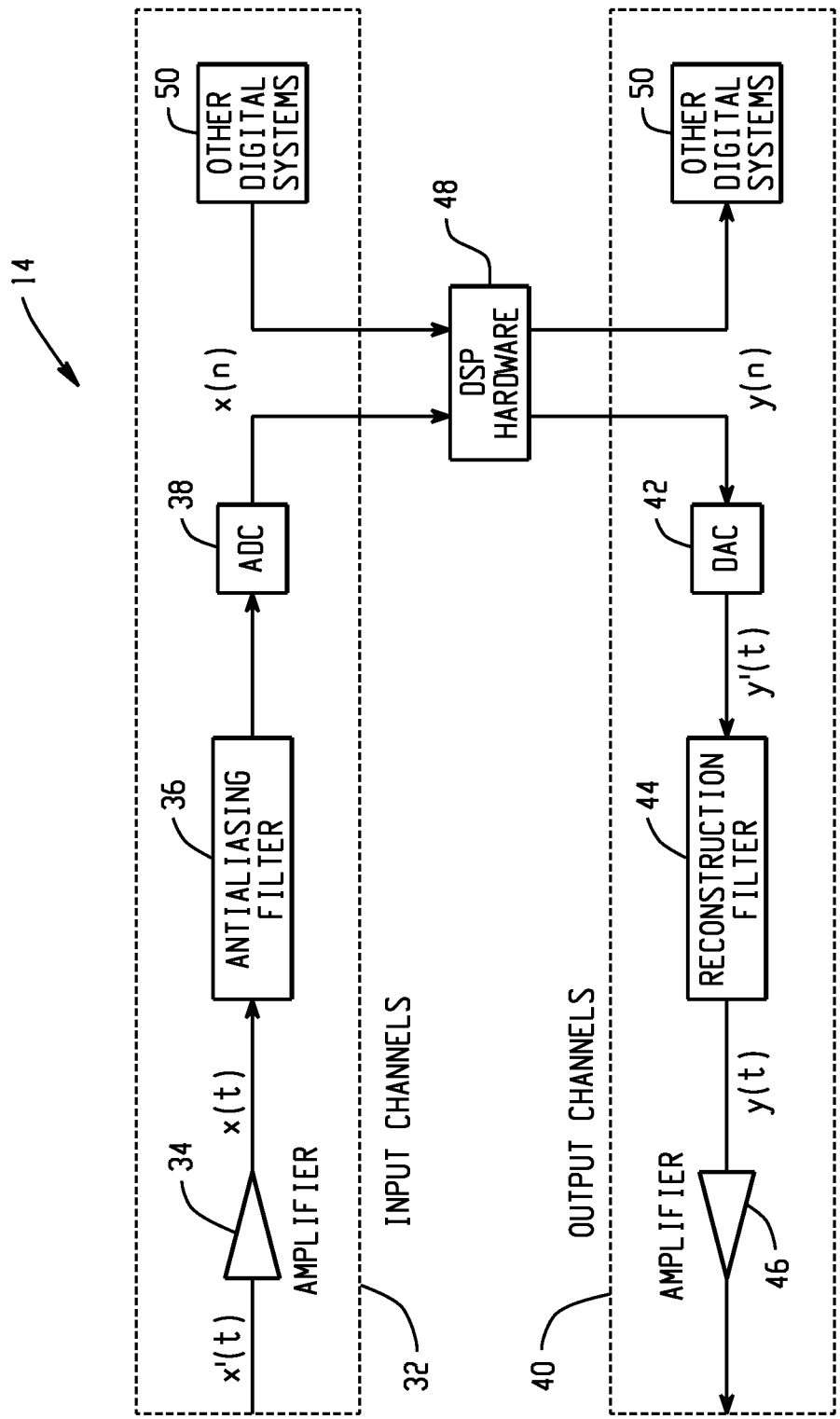
FIG. 3 is a block diagram of a controller unit.

The controller unit 14 is a signal processing unit for sending and receiving signals as well as processing and analyzing signals as shown in FIG. 3. The controller unit 14 includes various processing components such as, but not limited to, a power supply, amplifiers, computer processor with memory, and input/output channels. The controller unit 14 can optionally be enclosed by the pillow 18, or it can be located outside of the pillow 18.

The controller unit 14 further includes a power source 24. The power source 24 can be alternating current (AC) such as a cord to plug into a wall socket or direct current (DC) such as battery power, e.g., a rechargeable battery pack. Additionally, the power may be delivered wirelessly without man-made conductors, e.g., direct induction, resonant magnetic induction, electromagnetic radiation and electrical conduction through natural media.

There is at least one input channel 32. The number of input channels 32 is equal to the total number of error microphones 20 in the pillow unit 12 and reference microphones 52 in the reference sensing unit 16. The input channels 32 are analog, and include signal conditioning circuitry, a preamplifier 34 with adequate gain, an anti-aliasing low-pass filter 36, and an analog-to-digital converter (ADC) 38. The input channels 32 receive signals (or noise) from the error microphones 20 and the reference microphones 52.

There is at least one output channel 40. The number of output channels 40 is equal to the number of loudspeakers 22 in the pillow unit 12. The output channels 40 are analog, and include a digital-to-analog converter (DAC) 42, smoothing (reconstruction) low pass filter 44, and power amplifier 46 to drive the loudspeakers 22. The output channels 40 send a signal to the loudspeakers 22 to make sound.

A digital signal processing unit (DSP) 48 generally includes a processor with memory. The DSP receives signals from the input channels 32 and sends signals to the output channels 40. The DSP can also interface (i.e. input and output) with other digital systems 50, such as, but not limited to, audio players for entertainment, digital storage devices for sound recording and phone interfaces for hands-free communications.

The DSP also includes an algorithm for operation of the electronic pillow 10. In general, the algorithm controls interactions between the error microphones 20, the loudspeakers 22, and reference microphones 52. Preferably, the algorithm is one of (a) multiple-channel broadband feed forward active noise control for reducing noise, (b) adaptive acoustic echo cancellation for hands-free communication, (c) signal detection to avoid recording silence periods and sound recognition for non-invasive detection, or (d) integration of active noise control and acoustic echo cancellation. The DSP can also include other functions such as non-invasive monitoring using microphone signals and an alarm to wake the user 30 up or call caregivers for emergency situations. The DSP can also include the functions required for initiating the low pass filter volume modulation for incoming music and sound from the user's desired source. Exemplary algorithms for noise cancellation are disclosed in US Pat. Pub. No. 2013/0204617, incorporated herein by reference in its entirety.

The reference sensing unit 16 includes at least one reference microphone 52. Preferably, the reference microphones 52 are wireless for ease of placement, but they can also be wired. The reference microphones 52 are used to detect the particular noise that is desired to be abated and are therefore placed near that sound. For example, if the user 30 of the electronic pillow 10 wants to abate noises from other rooms that can be heard through their bedroom door, the reference microphone 52 can be placed directly on the bedroom door, for example. The reference microphone 52 can be placed near a snorer to abate a snoring noise, such as on the snorer's pillow, the snorer's blanket, on the wall above the snorer, or any other suitable place. If the pillow 18 is a headrest, the reference microphone 52 can be placed near any source of noise, or generally around the user 30 such as on the ceiling of a plane or car or headboard.

The electronic pillow 10 can be used for a variety of methods in conjunction with the algorithms. For example, the electronic pillow can be used in a method of abating unwanted noise by detecting an unwanted noise with a reference microphone, analyzing the unwanted noise, producing an anti-noise corresponding to the unwanted noise in a pillow, and abating the unwanted noise. Again, the reference microphone(s) 52 are placed wherever the noise to be abated is located. These reference microphones 52 detect the unwanted noise and the error microphones 20 detect the unwanted noise levels at the user's 30 location, both microphones 52 and 20 send signals to the input channels 32 of the controller unit 14, the signals are analyzed with an algorithm in the DSP, and signals are sent from the output channels 40 to the loudspeakers 22. The loudspeakers 22 then produce an anti-noise that abates the unwanted noise. With this method, the algorithm of multiple-channel broadband feed forward active noise control for reducing noise is used to control the electronic pillow 10.

The electronic pillow 10 can also be used in a method of hands-free communication by sending and receiving sound waves through a pillow in connection with a phone interface. The method operates essentially as described above; however, the error microphones 20 are used to detect speech and the loudspeakers are used to broadcast speech of the person that the user 30 is talking to. With this method, the algorithm of adaptive acoustic echo cancellation for hands-free communications is used to control the electronic pillow 10, and this algorithm can be combined with active noise control.

The electronic pillow can be used in a method of recording and monitoring sleep disorders, by recording noises produced by a sleeper with microphones encased within a pillow. Again, this method operates essentially as described above; however, the error microphones 20 are used to record sounds of the user 30 to diagnose sleep disorders. With this method, the algorithm of signal detection to avoid recording silence periods and sound recognition for non-invasive detection is used to control the electronic pillow 10.

The electronic pillow can further be used in a method of providing real-time response to emergencies by detecting a noise with a reference microphone in a pillow, analyzing the noise, and providing real-time response to an emergency indicated by the analyzed noise. The method is performed essentially as described above. Certain noises detected are categorized as potential emergency situations, such as, but not limited to, the cessation of breathing, extremely heavy breathing, choking sounds, and cries for help. Detecting such a noise prompts the performance of real-time response action, such as waking up the user 30 by producing a noise with the loudspeakers 22, or by notifying caregivers or emergency responders of the emergency. Notification can occur in conjunction with the hands-free communications features of the electronic pillow 10, i.e. by sending a message over telephone lines, or by any other warning signals sent to the caregivers.

The electronic pillow can also be used in a method of playing audio sound by playing audio sound through the loudspeakers 22 of the pillow unit 12. The audio sound can be any sound that the user 30 wants to hear, such as soothing music or nature sounds. The audio sound can also be sound from a television, stereo, entertainment system, or computer. This method can also be used to abate unwanted noise, as the audio sound masks snoring and environmental noises. Also, by embedding the loudspeakers 22 inside the pillow unit 12, lower volume can be used to play the audio sound for both noise cancellation and biofeedback, thus causing less interference with another bed partner.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A process for providing active noise cancellation and biofeedback in an electronic pillow comprising a pillow unit operatively coupled to a reference sensing unit and a controller unit, the process comprising:
   receiving signals via a plurality of error microphones encased in the pillow unit, wherein the error microphones are spaced a first predetermined distance from one another;
   receiving at least one signal from at least one reference sensing microphone in the reference sensing unit; and
   processing signals received from the error microphones and reference sensing microphone in the controller unit to simultaneously reduce noise and provide biofeedback in an area between the error microphones using a plurality of speakers encased in the pillow unit, wherein each of the speakers are spaced a second predetermined distance from each of the respective error microphones, wherein noise is reduced in the controller unit utilizing a multiple-channel feed-forward active noise control, and wherein the controller unit processes signals received from the at least one of the error microphones and the controller unit simultaneously provides both acoustic echo cancellation and biofeedback, wherein the biofeedback comprises emitting a sound at frequencies of less than 2.0 Hz by using constructive and/or destructive interference patterns of higher frequency sound waves or volume modulation of source content from at least one of the plurality of speakers.

2. The process of claim 1, wherein the controller unit comprises a digital signal processing unit operatively coupled to a phone interface, wherein the acoustic echo cancellation and the biofeedback is performed on signals received in the phone interface.

3. The process of claim 1, further comprising:
   using the at least one signal from the at least one reference sensing microphone to generate biofeedback, the biofeedback comprising an arrangement of music; and
   providing the biofeedback to the user.

4. The process of claim 1, further comprising:
   using the at least one signal from the at least one reference sensing microphone to generate biofeedback, the biofeedback comprising slow waves; and
   providing the biofeedback to the user.

5. The process of claim 1, wherein the electronic pillow is portable.

6. The process of claim 1, wherein the pillow is a headrest in a chair.

7. The process of claim 1, wherein the biofeedback provides an audible alarm responsive to an emergency situation of a user of the electronic pillow unit, wherein an emergency situation comprises at least one of a cessation of breathing by the user, irregular breathing of the user, and choking sounds of the user.

8. The process of claim 1, wherein the sound emitted at frequencies of less than 2.0 Hz is a beat frequency, wherein the beat frequency is monaural or binaural or isochronic.

9. The process of claim 8, wherein the isochronic beat frequency comprises a musical tone segment alternated with a silent segment to provide a frequency presentation rate of less than 2.0 Hz.

10. The process of claim 8, wherein emitting the monaural beat frequency comprises stacking two individual frequencies and combining the stacked frequencies into speaker channels of the plurality of speakers encased in the pillow unit to produce the beat frequency through each one of the speaker channels.

11. The process of claim 8, wherein emitting the binaural beat frequency comprises splitting frequency pairs into separate channels of at least two of the plurality of speakers.

12. The process of claim 8, wherein the beat frequency is embedded within other biofeedback.

13. The process of claim 12, wherein the other biofeedback is user defined music.

14. The process of claim 12, further comprising combining the beat frequency with key masking, wherein key masking comprises determining a musical key of the user defined music and adjusting base beat frequencies of the monoaural, binaural or isochronic beats so as to blend the monoaural, binaural or isochronic beat frequencies with the user defined music.

15. The process of claim 1, wherein the sound emitted is a beat frequency of less than 1.0 Hz.

16. A process for providing active noise cancellation and biofeedback in an electronic pillow comprising a pillow unit operatively coupled to a reference sensing unit and a controller unit, the process comprising:
   receiving signals via a plurality of error microphones encased in the pillow unit, wherein the error microphones are spaced a first predetermined distance from one another;
   receiving at least one signal from at least one reference sensing microphone in the reference sensing unit; and
   processing signals received from the error microphones and reference sensing microphone in the controller unit to simultaneously reduce noise and provide biofeedback in an area between the error microphones using a plurality of speakers encased in the pillow unit, where each of the speakers are spaced a second predetermined distance from each of the respective error microphones, wherein noise is reduced in the controller unit utilizing a multiple-channel feed-forward active noise control, and wherein the controller unit processes signals received from the at least one of the error microphones and the control unit simultaneously provides both acoustic echo cancellation and biofeedback, wherein the biofeedback comprises providing entrainment frequencies with user defined music, wherein providing the entrainment frequencies comprises key masking the user defined music by determining a musical key of the user defined music and adjusting base frequencies of the entrainment frequencies so as to blend the entrainment frequencies with the user defined music.

17. The process of claim 16, wherein the entrainment frequencies are less than 2.0 Hz.

18. The process of claim 16, wherein the entrainment frequencies are less than 1.0 Hz.

19. The process of claim 16, wherein the entrainment frequencies are monoaural or binaural or isochronic beat frequencies.

20. The process of claim 16, wherein determining the musical key of the user defined music comprises a fast fourier transform analysis measuring relative power of all frequencies captured within a recording of the user defined music.

21. The process of claim 20 further comprising superimposing a sine wave tone equivalent to a root note frequency of the musical key and a sine wave tone offset from the root note frequency by a specified frequency determined by a desired entrainment frequency.

* * * * *